United States Patent
Koch et al.

(10) Patent No.: US 6,642,248 B2
(45) Date of Patent: Nov. 4, 2003

(54) BENZO[B]PYRANO[3,2-H]ACRIDIN-7-ONE COMPOUNDS

(75) Inventors: Michel Koch, La Celle Saint Coud (FR); François Tillequin, Paris (FR); Sylvie Michel, Paris (FR); Elisabeth Seguin, Paris (FR); Abdelhakim El Omri, Rouen (FR); John Hickman, Paris (FR); Alain Pierre, Les Alluets le Roi (FR); Bruno Pfeiffer, Saint Leu la Foret (FR); Pierre Renard, Le Chesnay (FR)

(73) Assignee: Les Laboratories Servier, Neuilly-sur-Seine (FR)

( * ) Notice: Subject to any disclaimer, the term of this patent is extended or adjusted under 35 U.S.C. 154(b) by 0 days.

(21) Appl. No.: 10/205,566

(22) Filed: Jul. 25, 2002

(65) Prior Publication Data

US 2003/0073841 A1 Apr. 17, 2003

(30) Foreign Application Priority Data

Jul. 25, 2001 (FR) .............................. 01 09910

(51) Int. Cl.[7] .................. A61K 31/4741; C07D 491/52; C07D 491/153; A61P 35/00
(52) U.S. Cl. .................... 514/280; 514/279; 514/232.8; 514/211.09; 514/230.8; 546/41; 546/47; 544/125
(58) Field of Search ................ 514/280, 279, 514/232.8; 546/47, 41; 544/125

(56) References Cited

FOREIGN PATENT DOCUMENTS

WO    WO 9932491 A1 * 7/1999 ....... C07D/491/052

OTHER PUBLICATIONS

Hitotsuyanagi et al. Bioorganic & Medicinal Chemistry Letters. (1995) vol. 5, No. 10, pp. 1039–1042.*
Sof'ina et al. Experimental Evaluation of Antitumor Drugs in the USA and USSR and Clinical Correlations. NIH Publication No. 80–1933. (1980).*
Kraus–Berthier, L., Jan, M., Guilbaud, N., Naze, M., Pierré, A., and Atassi, G. Histology and Sensitivity to Anticancer Drugs of Two Human Non–Small Cell Lung Carcinomas Implanted in the Pleural Cavity of Nude Mice. Clinical Cancer Res., 6, 297–304, 2000.

Burbridge, M.F., Kraus–Berthier, L., Naze, M., Pierré, A., Atassi, G., and Guilbaud, N. Biological and Pharmacological Characterization of Three Models of Human Ovarian Carcinoma Established in Nude Mice: Use of the CA125 Tumour Marker to Predict Antitumour Activity. Int. J. Oncol., 15, 1155–1162, 1999.

* cited by examiner

*Primary Examiner*—Evelyn Mei Huang
(74) *Attorney, Agent, or Firm*—The Firm of Hueschen and Sage

(57) ABSTRACT

A compound selected from those of formula (I):

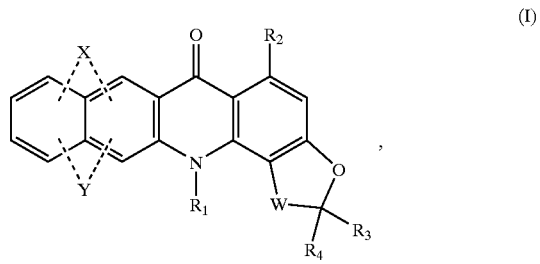

wherein:

X and Y represent group selected from hydrogen, halogen, mercapto, cyano, nitro, alkyl, trihaloalkyl, trihaloalkylcarbonylamino, —ORa, —NRaRb, —NRa—C(O)—$T_1$, —O—C(O)—$T_1$, —O—$T_2$-NRaRb, —O—$T_2$-ORa, —NRa—$T_2$-NRaRb, —NRa—$T_2$-ORa and —NRa—$T_2$-$CO_2$Ra wherein Ra, Rb, $T_1$, $T_2$ are as defined in the description, $R_1$ represents hydrogen or alkyl, $R_2$ represents a group selected from hydrogen, —ORa, —NRaRb, —NRa—C(O)—$T_1$, —O—C(O)—$T_1$, —O—$T_2$-NRaRb, —O—$T_2$-ORa, —NRa—$T_2$-NRaRb, —NRa—$T_2$-ORa and —NRa—$T_2$-$CO_2$Ra wherein Ra, Rb, $T_1$ and $T_2$ are as defined hereinbefore, $R_3$ and $R_4$ represent hydrogen or alkyl, W represents a group of formula —CH($R_5$)—CH($R_6$)—, —CH═C($R_7$)—, —C($R_7$)═CH— or —C(O)—CH($R_8$)— wherein $R_5$, $R_6$, $R_7$ and $R_8$ are as defined in the description, their isomers and N-oxides, and addition salts thereof with a pharmaceutically acceptable acid or base, and medicinal products containing the same which are useful in the treatment of cancer.

17 Claims, No Drawings

BENZO[B]PYRANO[3,2-H]ACRIDIN-7-ONE COMPOUNDS

The present invention relates to new benzo[b]pyrano[3,2-h]acridin-7-one compounds.

FIELD OF THE INVENTION

The compounds of the invention are derivatives of acronycine, an alkaloid which has anti-tumour properties that have been demonstrated in experimental models (*J. Pharm. Sci.*, 1966, 55 (8), 758–768). However, despite having quite a broad spectrum of activity, acronycine is of low potency and moderate activity. The solubility of the compound is, moreover, low, which limits its bioavailability, as well as its use in pharmaceutical compositions for administration by the intravenous route.

Various modifications have been made to the molecule, for example those described in *J. Med. Chem.*, 1996, 39, 4762–4766 or EP 1 042 326, allowing a significant improvement in the potency, anti-tumour efficacy and solubility of the products. Nevertheless, anti-cancer therapeutic requirements call for the constant development of new anti-tumour agents with the aim of obtaining medicaments that are simultaneously more active and better tolerated. More specifically, solid tumours constitute a major problem for anti-cancer chemotherapy because of their intrinsic and/or acquired resistance to existing compounds. Moreover, certain compounds which are shown to be highly active with respect to certain cell lines are found to be inactive with respect to other cell lines or indeed toxic. It is therefore of prime importance to have access to the widest range of compounds exhibiting powerful cytotoxic activity in order to have available the most effective treatments for the totality of tumour disorders, together with limited secondary effects and the longest desirable action over time.

Besides the fact that the compounds of the invention are new, they have surprising in vitro and in vivo activity which is greater than that observed hitherto. The compounds discovered by the Applicant accordingly have anti-tumour properties that make them especially useful in the treatment of cancers and, especially, of solid tumours.

DETAILED DESCRIPTION OF THE INVENTION

More specifically, the present invention relates to compounds of formula (I):

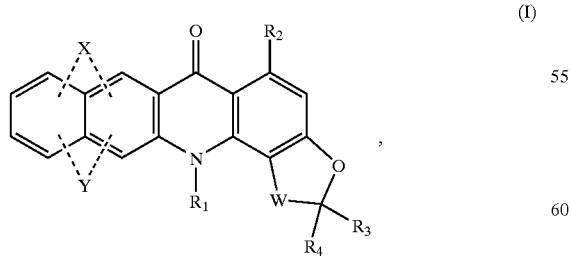

wherein:
X and Y, which may be the same or different, represent, independently of one another, a group selected from: hydrogen and halogen atoms,
mercapto, cyano, nitro, linear or branched ($C_1$–$C_6$) alkyl, linear or branched ($C_1$–$C_6$)-trihaloalkyl and linear or branched trihalo-($C_1$–$C_6$)alkyl-carbonylamino groups,
groups of formulae —ORa, —NRaRb, —NRa—C(O)-$T_1$, —O—C(O)-$T_1$, —O-$T_2$-NRaRb, —O-$T_2$-ORa, —NRa-$T_2$-NRaRb, —NRa-$T_2$-ORa and —NRa-$T_2$-$CO_2$Ra wherein:
Ra represents a group selected from a hydrogen atom and a linear or branched ($C_1$–$C_6$)alkyl group, an aryl group and an aryl-($C_1$–$C_6$)alkyl group wherein the alkyl moiety is linear or branched,
Rb represents a group selected from a hydrogen atom and a linear or branched ($C_1$–$C_6$)alkyl group, an aryl group and an aryl-($C_1$–$C_6$)alkyl group wherein the alkyl moiety is linear or branched, or Ra+Rb, together with the nitrogen atom carrying them, form a monocyclic 5- or 6-membered heterocycle optionally containing in the cyclic system a second hetero atom selected from oxygen and nitrogen,
$T_1$ represents a group selected from linear or branched ($C_1$–$C_6$)alkyl, linear or branched ($C_2$–$C_6$)alkenyl, aryl, aryl-($C_1$–$C_6$)alkyl (wherein the alkyl moiety is linear or branched), and a linear or branched ($C_1$–$C_6$)alkylene chain substituted by a group selected from —ORa and —NRaRb wherein Ra and Rb are as defined hereinbefore,
$T_2$ represents a linear or branched ($C_1$–$C_6$)alkylene chain,
or X and Y, when they are in adjacent positions, together form a methylenedioxy group or an ethylenedioxy group,
it being understood that the substituents X and Y may be present on either of the two adjacent benzene rings,
$R_1$ represents a hydrogen atom or a linear or branched ($C_1$–$C_6$)alkyl group,
$R_2$ represents a group selected from a hydrogen atom and linear or branched ($C_1$–$C_6$)alkyl, —ORa, —NRaRb, —NRa—C(O)-$T_1$, —O—C(O)-$T_1$, —O-$T_2$-NRaRb, —O-$T_2$-ORa, —NRa-$T_2$-NRaRb, —NRa-$T_2$-ORa and —NRa-$T_2$-$CO_2$Ra groups, wherein Ra, Rb, $T_1$ and $T_2$ are as defined hereinbefore,
$R_3$, $R_4$, which may be the same or different, represent, independently of one another, a hydrogen atom or a linear or branched ($C_1$–$C_6$)alkyl group,
W represents a group of formula —CH($R_5$)—CH($R_6$)—, —CH=C($R_7$)—, —C($R_7$)=CH— or —C(O)—CH($R_{d\,8}$)— wherein:
$R_5$ and/or $R_6$, represent(s) a group selected from —$W_1$—C($W_2$)—$W_3$-$T_1$, —$W_4$—C($W_2$)-$T'_1$, —$W_1$—S(O)$_n$—$W_3$-$T_1$ and —$W_1$—S(O)$_n$—$T_1$ wherein:
$W_1$ represents an oxygen or sulphur atom or a nitrogen atom substituted by a hydrogen atom or by a linear or branched ($C_1$–$C_6$)alkyl group, an aryl group or an aryl-($C_1$–$C_6$)alkyl group wherein the alkyl moiety is linear or branched,
$W_2$ represents an oxygen atom or a sulphur atom,
$W_3$ represents an oxygen or sulphur atom or a nitrogen atom substituted by a hydrogen atom or by a linear or branched $C_1$–$C_6$) alkyl group, an aryl group or an aryl-($C_1$–$C_6$)alkyl group wherein the alkyl moiety is linear or branched, a bond when $T_1$ represents a linear or branched ($C_2$–$C_6$) alkenyl group,
$W_4$ represents a sulphur atom or a nitrogen atom substituted by a hydrogen atom or by a linear or branched ($C_1$–$C_6$)alkyl group, an aryl group or an aryl-($C_1$–$C_6$)alkyl group wherein the alkyl moiety is linear or branched, $T_1$ is as defined hereinbefore, $T'_1$ represents a group selected from linear or branched ($C_2$–$C_6$)alkenyl, aryl, aryl-($C_1$–$C_6$)alkyl (wherein the alkyl moiety is linear or branched), a linear or branched ($C_1$–$C_6$)alkylene chain substituted by a group selected from —ORa and —NRaRb wherein Ra and Rb are as defined hereinbefore, n represents an integer selected from 1 and 2, and in the case where only one of the two groups $R_5$ and $R_6$ represents a group as defined hereinbefore then the other of the said groups $R_5$ or $R_6$ represents a group selected from a hydrogen atom, hydroxy, linear or branched ($C_1$–$C_6$)alkoxy, linear or branched ($C_1$–$C_6$) alkyl-carbonyloxy, arylcarbonyloxy, aryl-($C_1$–$C_6$) alkyl-carbonyloxy (wherein the alkyl moiety is linear or branched), and amino optionally substituted by one or two, identical or different, linear or branched ($C_1$–$C_6$)alkyl groups, $R_7$ represents a group selected from hydroxy, linear or branched ($C_1$–$C_6$)alkoxy, —C($W_2$)-$T_1$, —$W_1$—C($W_2$)—$W_3$-$T_1$, —$W_1$—C($W_2$)-$T_1$, —$W_1$—S(O)$_n$—$W_3$-$T_1$ and —$W_1$—S(O)$_n$—$T_1$ wherein $W_1$, $W_2$, $W_3$, $T_1$ and n are as defined hereinbefore, or $R_7$ may have the additional meaning of a hydrogen atom when $R_2$ represents a group —O-$T_2$-ORa and/or when X represents a hydrogen atom and Y, located in the 13-position of the naphthyl system of the pentacyclic skeleton, represents an amino group optionally substituted by one or two identical or different groups selected independently of one another from linear or branched ($C_1$–$C_6$)alkyl, linear or branched ($C_1$–$C_6$) acyl and linear or branched trihalo-($C_1$–$C_6$)alkyl-carbonyl, $R_8$ represents a linear or branched ($C_1$–$C_6$)alkoxy or linear or branched ($C_1$–$C_6$)alkyl-carbonyloxy group, or may have the additional meaning of hydroxy when $R_2$ represents a group —O-$T_2$-ORa as defined hereinbefore, to their enantiomers, diastereoisomers and N-oxides, and to addition salts thereof with a pharmaceutically acceptable acid or base.

Aryl is understood to mean a phenyl or naphthyl group optionally containing one or more, identical or different, substitutents selected from hydroxy, halogen, carboxy, nitro, amino, linear or branched ($C_1$–$C_6$)alkylamino, di($C_1$–$C_6$) alkylamino wherein each alkyl moiety may be linear or branched, linear or branched ($C_1$–$C_6$)alkoxy, linear or branched ($C_1$–$C_6$)acyl and linear or branched ($C_1$–$C_6$)alkyl-carbonyloxy.

Isomers are understood to comprise optical isomers, that is to say enantiomers and diastereoisomers.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, lysine etc.

Among the pharmaceutically acceptable bases there may be mentioned, without implying any limitation, sodium hydroxide, potassium hydroxide, triethylamine, tert-butylamine etc.

According to an advantageous embodiment of the invention, preferred compounds are compounds of formula (IA):

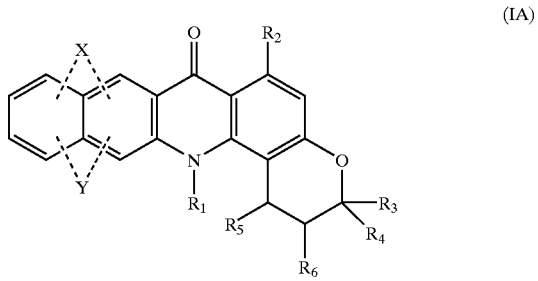

(IA)

wherein X, Y, $R_1$, $R_2$, $R_3$, $R_4$, $R_5$ and $R_6$ are as defined for formula (I).

Preferred compounds of formula (IA) are compounds wherein $R_5$ and $R_6$ are identical and each represent a group of formula —$W_1$—C($W_2$)—$W_3$-$T_1$ or —$W_1$—S(O)$_n$-$T_1$ wherein $W_1$, $W_2$, $W_3$, $T_1$ and n are as defined for formula (I).

In especially interesting manner, preferred compounds of formula (IA) are compounds wherein $R_5$ and $R_6$ are identical and each represent a group of formula —$W_1$—C($W_2$)—$W_3$-$T_1$ wherein $W_1$ represents an oxygen atom, $W_2$ represents an oxygen atom, $W_3$ represents a nitrogen atom substituted by a hydrogen atom, a linear or branched ($C_1$–$C_6$)alkyl group, an aryl group or an aryl-($C_1$–$C_6$)alkyl group wherein the alkyl moiety is linear or branched and $T_1$ is as defined for formula (I).

In another especially interesting manner, preferred compounds of formula (IA) are compounds wherein $R_5$ and $R_6$ are identical and each represent a group of formula —$W_1$—S(O)$_n$-$T_1$ wherein $W_1$ represents an oxygen atom, $T_1$ is as defined for formula (I) and n is equal to 2.

According to a second advantageous embodiment of the invention, preferred compounds are compounds of formula (IB):

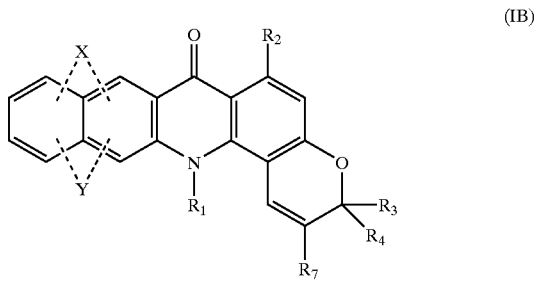

(IB)

wherein X, Y, $R_1$, $R_2$, $R_3$, $R_4$ and $R_7$ are as defined for formula (I).

Preferred compounds of formula (IB) are compounds wherein $R_7$ represents a group selected from —C($W_2$)-$T_1$ and —$W_1$—C($W_2$)-$T_1$ wherein $W_1$, $W_2$ and $T_1$ are as defined for formula (I).

In especially interesting manner, preferred compounds of formula (IB) are compounds wherein $W_1$ represents an oxygen atom, $W_2$ represents an oxygen atom and $T_1$ represents a linear or branched ($C_1$–$C_6$)alkyl group, an aryl group or an aryl-($C_1$–$C_6$)alkyl group wherein the alkyl moiety is linear or branched.

According to a third advantageous embodiment of the invention, preferred compounds are compounds of formula (IC):

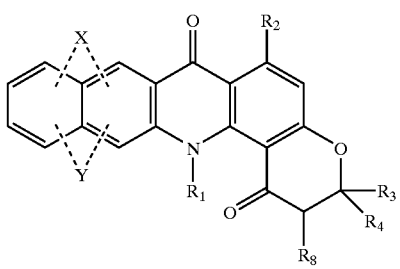

wherein X, Y, $R_1$, $R_2$, $R_3$, $R_4$ and $R_8$ are as defined for formula (I).

Substituents $R_3$ and $R_4$ that are preferred according to the invention are linear or branched ($C_1$–$C_6$)alkyl groups.

Substituents $R_2$ that are preferred according to the invention are groups selected from linear or branched ($C_1$–$C_6$) alkoxy, —NRaRb, —O-$T_2$-NRaRb, —O-$T_2$-ORa, —NRa-$T_2$-NRaRb and —NRa-$T_2$-ORa wherein Ra, Rb, $T_1$ and $T_2$ are as defined for formula (I).

According to a fourth advantageous embodiment of the invention, preferred compounds are compounds of formula ($IB_1$):

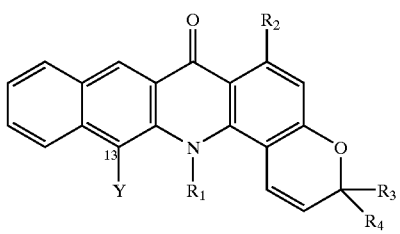

wherein $R_1$, $R_2$, $R_3$ and $R_4$ are as defined for formula (IB) and Y represents an amino group optionally substituted by one or two identical or different groups selected independently of one another from linear or branched ($C_1$–$C_6$)alkyl, linear or branched ($C_1$–$C_6$)acyl and linear or branched trihalo-($C_1$–$C_6$)alkyl-carbonyl.

In especially advantageous manner, preferred compounds of the invention are:

(1S,2S)-1-{[(dimethylamino)carbonyl]oxy}-6-methoxy-3,3,14-trimethyl-7-oxo-2,3,7,14-tetrahydro-1H-benzo[b]pyrano[3,2-h]acridin-2-yl dimethylcarbamate, (1S,2S)-6-methoxy-3,3,14-trimethyl-2-{[(4-methylphenyl)sulphonyl]oxy}-7-oxo-2,3,7,14-tetrahydro-1H-benzo[b]pyrano[3,2-h]acridin-1-yl 4-methylbenzenesulphonate, 6-methoxy-3,3,14-trimethyl-7-oxo-7,14-dihydro-3H-benzo[b]pyrano[3,2-h]acridin-2-yl acetate, 2-benzoyl-6-methoxy-3,3,14-trimethyl-3,14-dihydro-7H-benzo[b]pyrano[3,2-h]-acridin-7-one 2-butyryl-6-methoxy-3,3,14-trimethyl-3,14-dihydro-7H-benzo[b]pyrano[3,2-h]-acridin-7-one, 2-acetyl-6-methoxy-3,3,14-trimethyl-3,14-dihydro-7H-benzo[b]pyrano[3,2-h]-acridin-7-one, 6-methoxy-3,3,14-trimethyl-7-oxo-7,14-dihydro-3H-benzo[b]pyrano[3,2-h]-acridin-2-yl butyrate, 6-(2-hydroxyethoxy)-3,3,14-trimethyl-3,14-dihydro-7H-benzo[b]pyrano[3,2-h]-acridin-7-one, 13-amino-6-methoxy-3,3,14-trimethyl-3,14-dihydro-7H-benzo[b]pyrano[3,2-h]-acridin-7-one, N-(6-methoxy-3,3,14-trimethyl-7-oxo-7,14-dihydro-3H-benzo[b]pyrano[3,2-h]-acridin-13-yl)acetamide, 6-methoxy-3,3-dimethyl-1,7-dioxo-2,3,7,14-tetrahydro-1H-benzo[b]pyrano[3,2-h]-acridin-2-yl acetate.

The enantiomers, diastereoisomers, N-oxides and addition salts with a pharmaceutically acceptable acid or base of the preferred compounds form an integral part of the invention.

The present invention relates also to a process for the preparation of compounds of formula (I), which process is characterised in that there is used as starting material the compound of formula (VI):

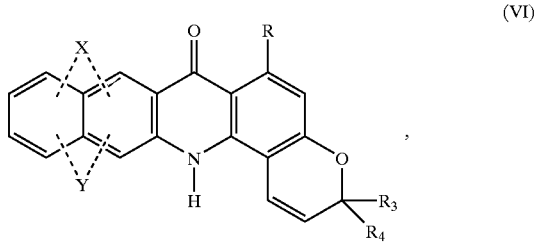

wherein X, Y, R, $R_3$ and $R_4$ are as defined hereinbefore, the nitrogen atom of which compound of formula (VI) is optionally substituted, by the action of an alkyl halide or of a dialkyl sulphate in the presence of a deprotonating agent, in an aprotic polar solvent or under phase transfer conditions, yielding the compounds of formula (IX):

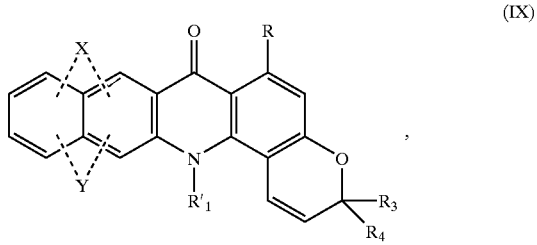

wherein X, Y, R, $R_3$ and $R_4$ are as defined hereinbefore and $R'_1$ represents a linear or branched ($C_1$–$C_6$)alkyl group, which compounds of formula (IX) are subjected to the action of an alkylating agent or an acylating agent under customary conditions of organic synthesis to yield the compounds of formula (X):

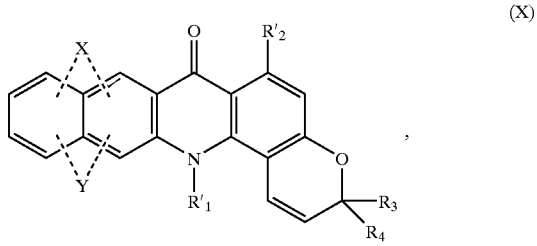

wherein X, Y, $R'_1$, $R_3$ and $R_4$ are as defined hereinbefore and $R'_2$ represents a group selected from —ORa, —O—C(O)-$T_1$, —O-$T_2$-NRaRb and —O-$T_2$-ORa wherein Ra, Rb, $T_1$ and $T_2$ are as defined for formula (I), which compounds of formula (X), in the case where $R'_2$ represents an alkoxy group, are treated with a compound of formula (XI):

  (XI), wherein Ra represents a hydrogen atom, a linear or branched $(C_1-C_6)$alkyl group, an aryl group or an aryl-$(C_1-C_6)$alkyl group wherein the alkyl moiety is linear or branched, and $R_{10}$ represents a group selected from Rb, —C(O)-$T_1$, -$T_2$-NRaRb, -$T_2$-ORa and -$T_2$-$CO_2$Ra wherein Ra, Rb, $T_1$ and $T_2$ are as defined for formula (I), to yield the compounds of formula (XII):

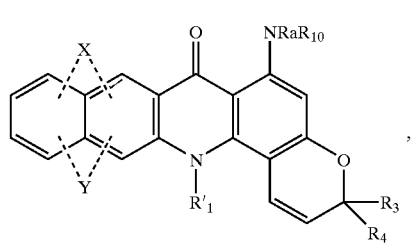  (XII)

wherein X, Y, $R'_1$, $R_3$, $R_4$, Ra and $R_{10}$ are as defined hereinbefore, the totality of the compounds of formulae (VI), (IX), (X) and (XII) forming the compounds of formula (XIII):

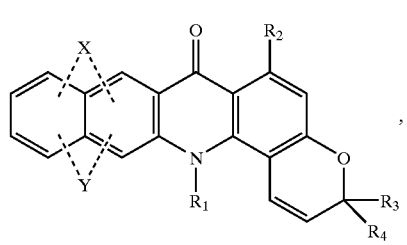  (XIII)

wherein X, Y, $R_1$, $R_2$, $R_3$ and $R_4$ are as defined in the general definition for formula (I), which compounds of formula (XIII) are subjected:

a) ⇒either to the action of a compound of formula (XIV):

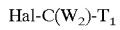  (XIV), wherein Hal represents a halogen atom and $W_2$ and $T_1$ are as defined in the general definition for formula (I), to yield the compounds of formula (I/a), a particular case of the compounds of formula (I):

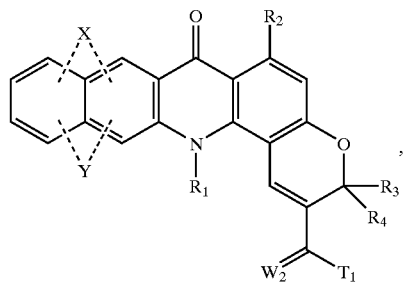  (I/a)

wherein X, Y, $R_1$, $R_2$, $R_3$, $R_4$, $W_2$ and $T_1$ are as defined hereinbefore, b) ⇒or to the action of an oxidising agent for alkene functions to yield the compounds of formula (XV):

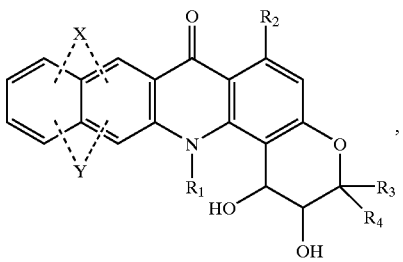  (XV)

wherein X, Y, $R_1$, $R_2$, $R_3$ and $R_4$ are as defined hereinbefore, which compounds of formula (XV) are treated with a compound of formula (XVI):

  (XVI), wherein Hal represents a halogen atom and $G_1$ represents a group selected from —C($W_2$)—$W_3$-$T_1$, —C($W_2$)-$T_1$, —S(O)$_n$—$W_3$-$T_1$ and —S(O)$_n$-$T_1$ wherein $W_2$, $W_3$, $T_1$ and n are as defined for formula (I), to yield the compounds of formulae (I/b), (I/c) and (I/d), particular cases of the compounds of formula (I):

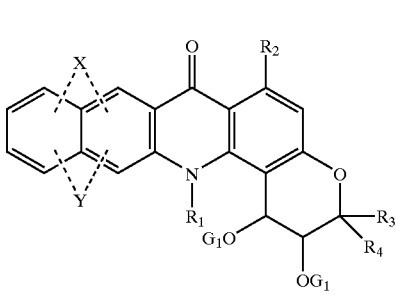  (I/b)

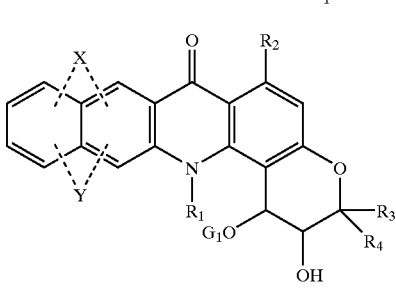  (I/c)

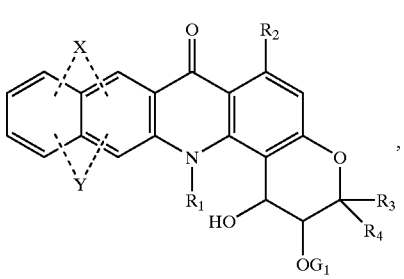  (I/d)

wherein X, Y, $R_1$, $R_2$, $R_3$, $R_4$ and $G_1$ are as defined hereinbefore, which compounds of formulae (I/c) and/or (I/d) are subjected:

either to the action of an alcohol of formula $R_{20}$—OH, wherein $R_{20}$ represents a linear or branched ($C_1$–$C_6$) alkyl group, to yield the compounds of formulae (I/c1) and (I/d1), respectively:

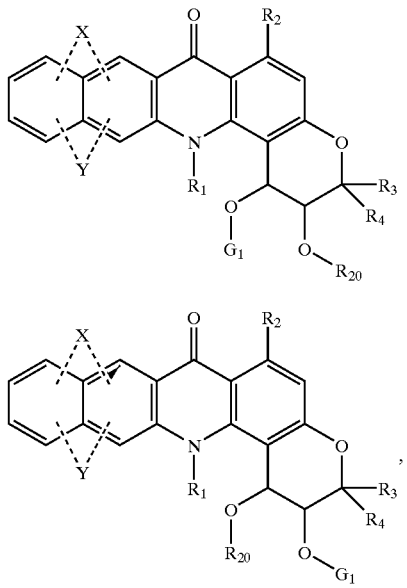

(I/c1)

(I/d1)

wherein X, Y, $R_1$, $R_2$, $R_3$, $R_4$, $G_1$ and $R_{20}$ are as defined hereinbefore, or to the action of an anhydride of formula $(R_{30}CO)_2O$, wherein $R_{30}$ represents a linear or branched ($C_1$–$C_6$) alkyl group, an aryl group or an aryl-($C_1$–$C_6$)alkyl group wherein the alkyl moiety is linear or branched, to yield the compounds of formulae (I/c2) and (I/d2), respectively:

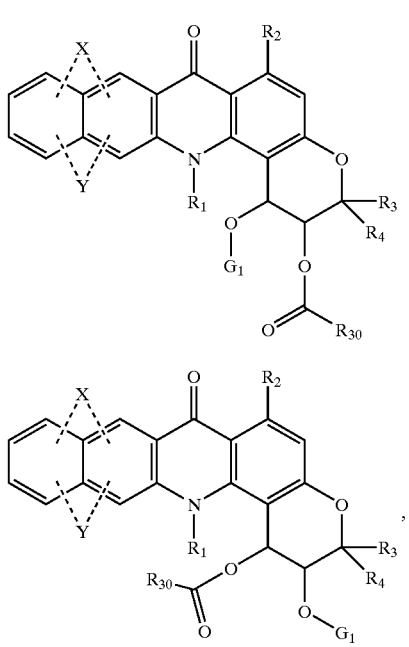

(I/c2)

(I/d2)

wherein X, Y, $R_1$, $R_2$, $R_3$, $R_4$, $G_1$ and $R_{30}$ are as defined hereinbefore, or to dehydrating conditions in an acid medium to yield the compounds of formulae (I/c3) and (I/d3), respectively, particular cases of the compounds of formula (I):

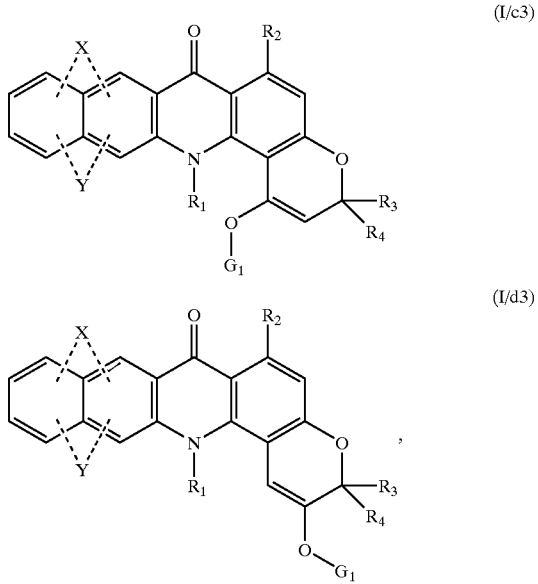

(I/c3)

(I/d3)

wherein X, Y, $R_1$, $R_2$, $R_3$, $R_4$ and $G_1$ are as defined hereinbefore, c) ⇒or to the action of a peracid or of dimethyl dioxirane to yield the compounds of formula (XVII):

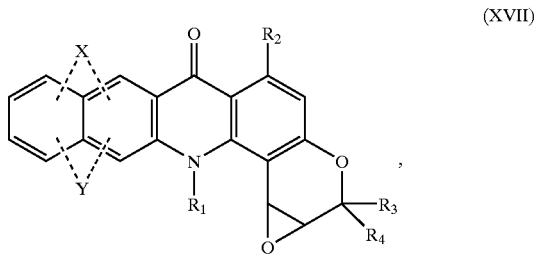

(XVII)

wherein X, Y, $R_1$, $R_2$, $R_3$ and $R_4$ are as defined hereinbefore, which compounds of formula (XVII) are treated with ammoniac or with a primary amine to yield the compounds of formulae (XVIII/a) and/or (XVIII/b):

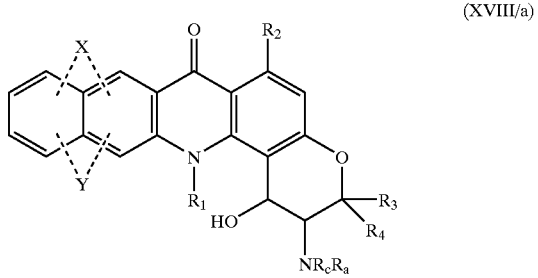

(XVIII/a)

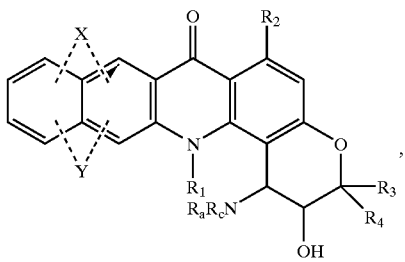

(XVIII/b)

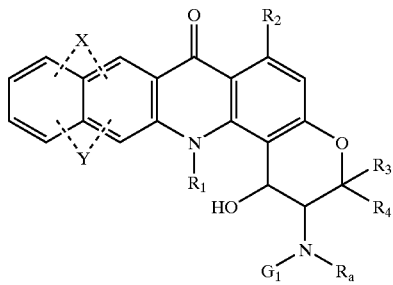

(I/e1)

wherein X, Y, $R_1$, $R_2$, $R_3$ and $R_4$ are as defined hereinbefore, $R_c$ represents a hydrogen atom and $R_a$ represents a hydrogen atom in the case where the reagent used is ammoniac or represents a group selected from linear or branched ($C_1$–$C_6$) alkyl, aryl and aryl-($C_1$–$C_6$)alkyl (wherein the alkyl moiety is linear or branched) in the case where the reagent used is a primary amine, the alcohol function of which compounds of formulae (XVIII/a) and (XVIII/b) is protected by a protecting group for hydroxy groups, the compounds then being subjected to the action of a compound of formula Hal-$G_1$ (XVI) as defined hereinbefore to yield the compounds of formulae (XIX/a) and (XIX/b), respectively,

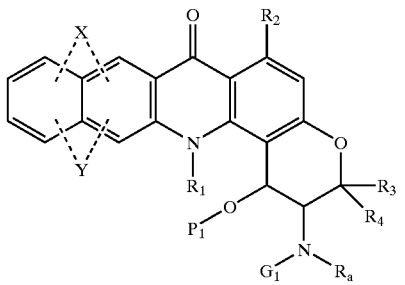

(XIX/a)

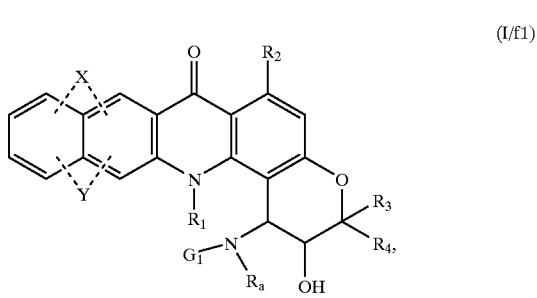

(I/f1)

wherein X, Y, $R_1$, $R_2$, $R_3$, $R_4$, $R_a$ and $G_1$ are as defined hereinbefore, which compounds of formulae (I/e1) and (I/f1) are subjected:
either to the action of an anhydride of formula $(R_{30}CO)_2O$, wherein $R_{30}$ represents a linear or branched ($C_1$–$C_6$)alkyl group, an aryl group or an aryl-($C_1$–$C_6$)alkyl group wherein the alkyl moiety is linear or branched, to yield the compounds of formulae (I/e2) and (If2), respectively, particular cases of the compounds of formula (1):

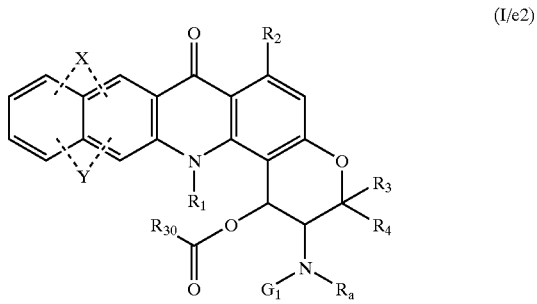

(I/e2)

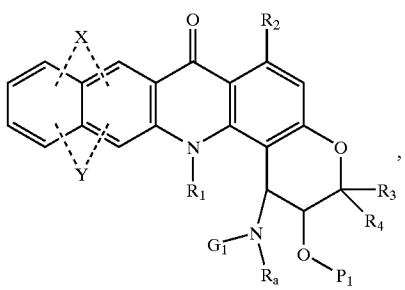

(XIX/b)

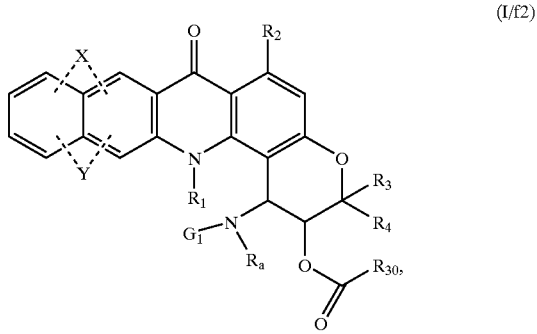

(I/f2)

wherein X, Y, $R_1$, $R_2$, $R_3$, $R_4$, $R_a$ and $G_1$ are as defined hereinbefore and $P_1$ represents a protecting group for hydroxy functions, the hydroxy group of which compounds of formulae (XIX/a) and (XIX/b) is deprotected to yield the compounds of formulae (I/e1) and (I/f1), respectively, particular cases of the compounds of formula (I):

wherein X, Y, $R_1$, $R_2$, $R_3$, $R_4$, $R_a$, $G_1$ and $R_{30}$ are as defined hereinbefore,
or to dehydrating conditions in an acid medium to yield the compounds of formulae (I/e3) and (I/f3), respectively, particular cases of the compounds of formula (I):

(I/e3)
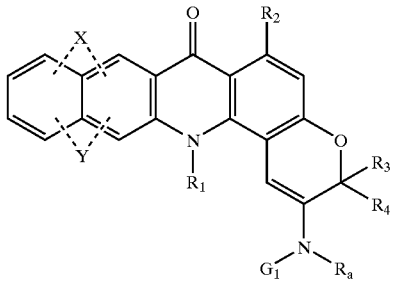

(I/f3)
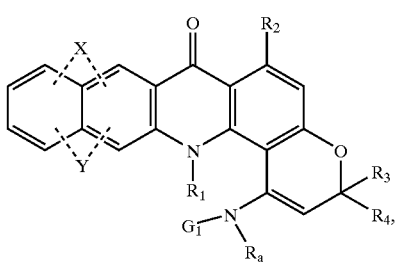

wherein X, Y, $R_1$, $R_2$, $R_3$, $R_4$, $R_a$ and $G_1$ are as defined hereinbefore, d) ⇒ or to the action of $NaN_3$ in the presence of hydrogen peroxide, followed by a reduction step using tri-n-butyltin hydride, for example, to yield the compounds of formula (XX):

(XX)
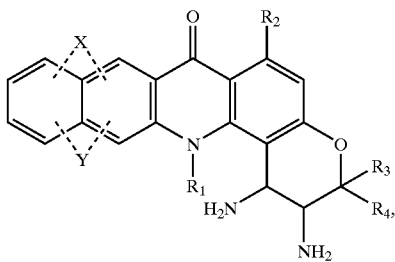

wherein X, Y, $R_1$, $R_2$, $R_3$ and $R_4$ are as defined hereinbefore, which compounds of formula (XX) are subjected to the action of a compound of formula Hal-$G_1$ (XVI) as defined hereinbefore to yield the compounds of formula (I/g), a particular case of the compounds of formula (I):

(I/g)
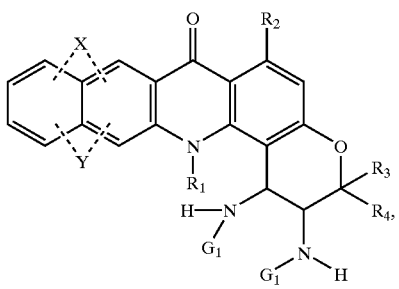

wherein X, Y, $R_1$, $R_2$, $R_3$, $R_4$ and $G_1$ are as defined hereinbefore, e) ⇒ or to the action of potassium permanganate in a polar medium to yield the compounds of formula (XXI):

(XXI)
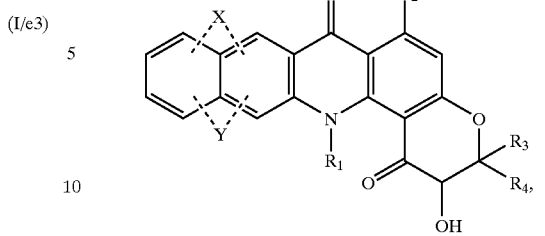

wherein X, Y, $R_1$, $R_2$, $R_3$ and $R_4$ are as defined hereinbefore, which compounds of formula (XXI) are subjected to the action of either an alkylating agent or an acylating agent to yield the compounds of formula (I/h), a particular case of the compounds of formula (I):

(I/h)
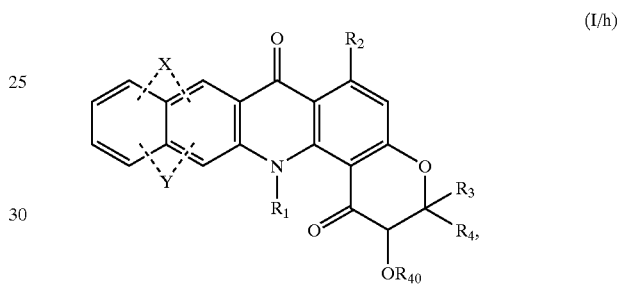

wherein X, Y, $R_1$, $R_2$, $R_3$ and $R_4$ are as defined hereinbefore and $R_{40}$ represents a linear or branched $(C_1-C_6)$alkyl group or a linear or branched $(C_1-C_6)$acyl group, or the hydroxy functions of which compounds of formula (XXI) are protected with a protecting group conventionally used in organic synthesis, the compounds then being subjected to the action of $P_2S_5$ to yield the compounds of formula (XXII):

(XXII)
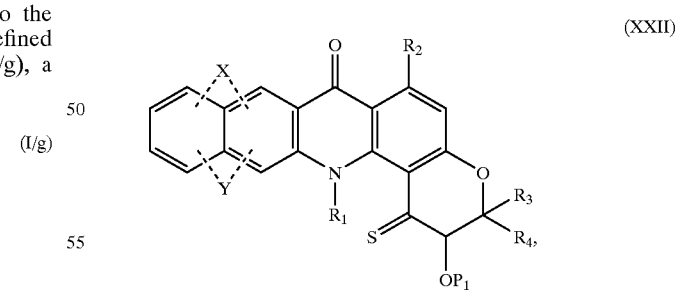

wherein X, Y, $R_1$, $R_2$, $R_3$ and $R_4$ are as defined hereinbefore and $P_1$ represents a protecting group for hydroxy functions, which compounds of formula (XXII) are treated with a reducing agent and then subjected to a reaction for deprotection of the hydroxy function to yield the compounds of formula (XXIII):

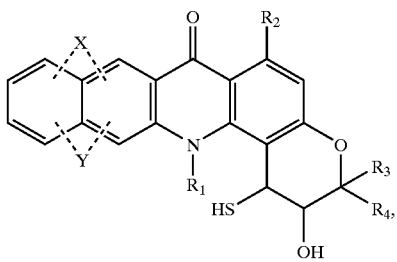

(XXIII)

wherein X, Y, $R_1$, $R_2$, $R_3$ and $R_4$ are as defined hereinbefore, which compounds of formula (XXIII) are treated with a compound of formula (XVI) as defined hereinbefore to yield the compounds of formula (I/i), a particular case of the compounds of formula (I):

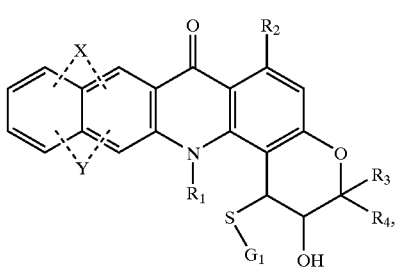

(I/i)

wherein X, Y, $G_1$, $R_1$, $R_2$, $R_3$ and $R_4$ are as defined hereinbefore,
which compounds of formula (I/i) may be subjected to the action of an alkylating agent, an acylating agent or a compound of formula (XVIa):

Hal-$G'_1$ (XVIa), wherein Hal represents a halogen atom and $G'_1$ represents a group selected from —C($W_2$)—$W_3$-$T_1$, —C($W_2$)-$T_1$, —S(O)$_n$—$W_3$-$T_1$ and —S(O)$_n$-$T_1$, wherein $W_2$, $W_3$, $T_1$ and n are as defined for formula (I),
to yield the compounds of formula (I/j), a particular case of the compounds of formula (I):

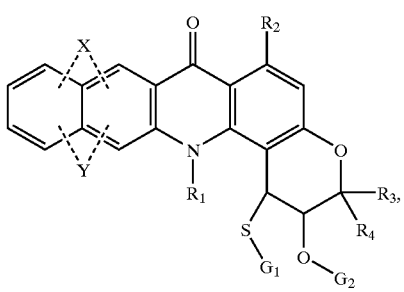

(I/j)

wherein X, Y, $G_1$, $R_1$, $R_2$, $R_3$ and $R_4$ are as defined hereinbefore and $G_2$ represents a group selected from $G'_1$ as defined hereinbefore, linear or branched ($C_1$–$C_6$)alkoxy, linear or branched ($C_1$–$C_6$)alkyl-carbonyloxy, arylcarbonyloxy and aryl-($C_1$–$C_6$)alkyl-carbonyloxy (wherein the alkyl moiety is linear or branched),
the compounds of formulae (I/a) to (I/j), (I/$c_1$) to (I/$c_3$), (I/$d_1$) to (I/$d_3$), (I/$e_1$) to (I/$e_3$) and (I/$f_1$) to (I/$f_3$) constituting the totality of the compounds of the invention, which are purified, if necessary, according to a conventional purification technique, which may be, if desired, separated into their different isomers according to a conventional separation technique and which are converted, if desired, into their N-oxides and, where appropriate, their addition salts with a pharmaceutically acceptable acid or base.

The compounds of formula (VI) may advantageously be obtained:

either starting from 3-amino-2-naphthalenecarboxylic acid compounds (II):

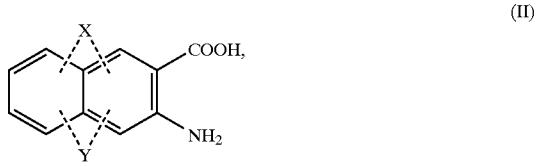

(II)

wherein X and Y are as defined for formula (I), which are reacted with a phloroglucinol compound of formula (III):

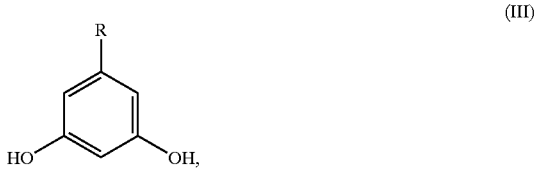

(III)

wherein R represents a hydrogen atom, a hydroxy group or a linear or branched ($C_1$–$C_6$)alkyl group, to yield the compounds of formula (IV):

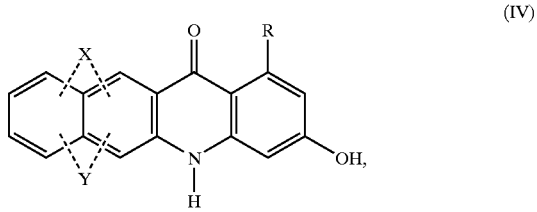

(IV)

wherein X, Y and R are as defined hereinbefore, which are then treated under basic conditions in an aprotic solvent with an alkyne of formula (V):

(V)

wherein Hal represents a halogen atom and $R_3$ and $R_4$ are as defined for formula (I), to yield the compounds of formula (VI) as defined hereinbefore, or starting from 3-halo-2-naphthalenecarboxylic acid compounds of formula (VII):

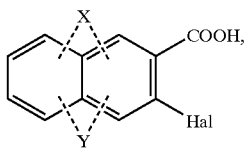

(VII)

wherein X and Y are as defined for formula (I) and Hal represents a halogen atom,
which are reacted with an amino-chromene compound of formula (VIII):

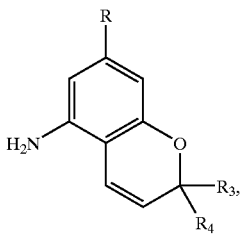

(VIII)

wherein $R_3$ and $R_4$ are as defined for formula (I) and R is as defined hereinbefore,
to yield, likewise, the compounds of formula (VI) as defined hereinbefore.

The compounds of formula (XIII) are synthesis intermediates that are useful in obtaining the compounds of formula (I). Among those compounds of formula (XIII) there are distinguished:

compounds of formula ($IB_1$):

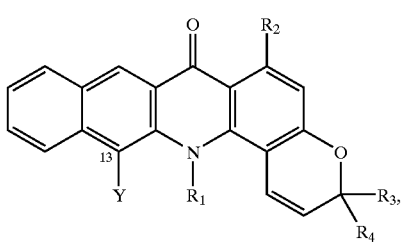

($IB_1$)

wherein $R_1$, $R_2$, $R_3$ and $R_4$ are as defined for formula (IB) and Y represents an amino group optionally substituted by one or two identical or different groups selected independently of one another from linear or branched ($C_1$–$C_6$)alkyl, linear or branched ($C_1$–$C_6$)acyl and linear or branched trihalo-($C_1$–$C_6$)alkyl-carbonyl,
and compounds of formula ($IB_2$):

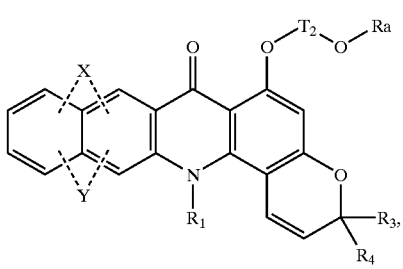

($IB_2$)

wherein $R_1$, $R_3$, $R_4$, $T_2$, Ra, X and Y are as defined for formula (I).

Those compounds of formulae ($IB_1$) and ($IB_2$) are new and have cytotoxic activity. They are therefore useful in the treatment of cancers.

The compounds of formula (XXI) likewise are synthesis intermediates that are useful in obtaining the compounds of formula (I) and, more especially, compounds of formula (IC). Those compounds of formula (XXI) likewise have cytotoxic activity. Their use as an active ingredient in a pharmaceutical composition makes the latter useful in the treatment of cancers.

The compounds of formulae (II), (III), (V), (VII), (VIII), (XI), (XIV) and (XVI) either are commercially available compounds or are obtained according to conventional methods of organic synthesis well known to the person skilled in the art.

The compounds of formula (I) have especially valuable anti-tumour properties. They have excellent in vitro cytotoxicity with respect to cell lines originating from murine and human tumours, by virtue of specific blockage of the cell cycle, and are active in vivo, in the mouse, with respect to transplantable murine and human tumours. The characteristic properties of these compounds allow them to be used therapeutically as anti-tumour agents.

The present invention relates also to pharmaceutical compositions comprising, as active ingredient, at least one compound of formula (I), an enantiomer or diastereoisomer thereof, or an N-oxide thereof, or an addition salt thereof with a pharmaceutically acceptable acid or base, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspensions or emulsions and also sterile powders for reconstituting injectable solutions or dispersions.

Pharmaceutical compositions according to the invention for solid oral administrations especially include tablets or dragees, sublingual tablets, sachets, gelatin capsules and granules, and for liquid oral, nasal, buccal or ocular administrations especially include emulsions, solutions, suspensions, drops, syrups and aerosols.

Pharmaceutical compositions for rectal or vaginal administration are preferably suppositories and those for per- or trans-cutaneous administration especially include powders, aerosols, creams, ointments, gels and patches.

The pharmaceutical compositions mentioned hereinbefore illustrate the invention but do not limit it in any way.

Among the inert, non-toxic, pharmaceutically acceptable excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colourants, aromatising agents etc.

The useful dosage varies according to the age and weight of the patient, the administration route, the pharmaceutical composition used, the nature and severity of the disorder and the administration of any associated treatments. The dosage ranges from 0.1 mg to 1000 mg per day in one or more administrations.

The Examples that follow illustrate the invention but do not limit it in any way.

The starting materials used are products that are known or that are prepared according to known operating procedures. The various Preparations yield synthesis intermediates that are useful in preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given refers to the salt form of the compound.

Preparation 1

6-Methoxy-3,3,14-trimethyl-7,14-dihydro-3H-benzo [b]pyrano-[3,2-h]acridin-7-one

Step A: 1,3-Dihydroxy-5,12-dihydro-benzo[b]acridin-12-one

To a solution of 5 g of 3-amino-2-naphthalenecarboxylic acid in 50 ml of heptan-1-ol there are added 3.5 g of 1,3,5-trihydroxybenzene and 62.5 mg of para-toluenesulphonic acid. The mixture is stirred for 48 hours under reflux using a Dean-Stark apparatus, and the reaction mixture is then concentrated in vacuo. The residue is chromatographed over silica gel (eluant:cyclohexane/acetone: 90/10). The isolated product is crystallised from a cyclohexane/acetone mixture, allowing 5.2 g of the expected product to be obtained.

Step B: 6-Hydroxy-3,3-dimethyl-7,14-dihydro-3H-benzo[b] pyrano[3,2-h]acridin-7-one To a solution of 2 g of the product of Step A in 50 ml of anhydrous dimethylformamide, under an inert atmosphere, there are added 2 g of anhydrous potassium carbonate. After stirring for 15 minutes at 65° C., 2.4 g of anhydrous potassium iodide and 4.4 g of 3-chloro-3-methyl-1-butyne are added, and the reaction mixture is held at 65° C. for 24 hours and then at 130° C. for 1 hour. After cooling, the solution is hydrolysed and then extracted with dichloromethane. The combined organic phases are washed with water and then with 1M potassium hydroxide solution, dried over sodium sulphate and then evaporated. After chromatography over silica gel (cyclohexane/acetone: 90/10), 1.10 g of the expected product are isolated.

Melting point: 225° C.

Step C: 6-Methoxy-3,3,14-trimethyl-7,14-dihydro-3H-benzo[b]pyrano-[3,2-h]acridin-7-one To a solution of 0.5 g of the product obtained in Step B in 20 ml of anhydrous dimethylformamide there are slowly added, at 0° C., under an inert atmosphere, 0.16 g of sodium hydride and then, after 15 minutes, 0.65 ml of dimethyl sulphate (6 equivalents). After 1 hour, the reaction mixture is hydrolysed using ice and is then extracted with ethyl acetate. After washing the organic phase with aqueous sodium hydroxide solution, it is dried over sodium sulphate and then evaporated in vacuo. Chromatography over silica gel (cyclohexane/acetone: 98/2) allows 0.42 g of the expected product to be obtained. Melting point: 188° C.

Preparation 2

(±)-cis-1,2-Dihydroxy-6-methoxy-3,3,14-trimethyl-2,3,7,14-tetra-hydro-1H-benzo[b]pyrano[3,2-h] acridin-7-one To a solution of 2 g of the product of Preparation 1 and 0.9 g of 4-methylmorpholine-N-oxide monohydrate in 40 ml of a mixture of tert-butanol/tetrahydrofuran/water (10/3/1) there is added osmium tetroxide in the form of a 2.5% solution in 3.8 ml of 2-methyl-2-propanol. After 2 days at ambient temperature, 105 ml of saturated $NaHSO_3$ solution are added, and the mixture is stirred for 1 hour and then extracted with dichloromethane. The combined organic phases are dried over sodium sulphate and concentrated in vacuo. Chromatography over silica gel (dichloromethane/methanol: 95/5) allows 1.3 g of the expected product to be isolated.

Melting point: 194° C.

Preparation 3

6-(Diethylaminopropylamino)-3,3,14-trimethyl-7, 14-dihydro-3H-benzo[b]pyrano[3,2-h]acridin-7-one To 0.15 g of the product of Preparation 1 there are added 4 ml of N,N-diethyl-propylenediamine. After reacting for 5 days at 70° C. under an inert atmosphere, the reaction mixture is evaporated under reduced pressure. The residue obtained is chromatographed over silica gel (cyclohexane/ethyl acetate: 80/20), allowing the expected product to be isolated.

Mass spectrum: (DIC/$NH_3$): m/z: 470 (M+H)$^+$

Preparation 4

6-[(2-Morpholin-4-yl)ethylamino]-3,3,14-trimethyl-7,14-dihydro-3H-benzo[b]pyrano[3,2-h]acridin-7-one The procedure is as in Preparation 3, using 4-(2-aminoethyl)-morpholine as reagent.

Mass spectrum: (DIC/$NH_3$): m/z: 470 (M+H)$^+$

Preparation 5

(±)-cis-1,2-Dihydroxy-6-(diethylaminopropylamino)-3,3,14-trimethyl-2,3,7, 14-tetrahydro-1H-benzo[b]pyrano[3,2-h]acridin-7-one The procedure is as in Preparation 2, using the compound of Preparation 3 as substrate.

Preparation 6

(±)-1-Amino-2-hydroxy-6-methoxy-3,3,14-trimethyl-2,3,7,14-tetrahydro-1H-benzo[b]pyrano[3, 2-h]acridin-7-one Step A: (±)-1-Azido-2-hydroxy-6-methoxy-3,3,14-trimethyl-2,3,7,14-tetrahydro-1H-benzo[b]pyrano[3,2-h] acridin-7-one To a solution of 0.15 g of the compound of Preparation 2 and 0.5 g of $NaN_3$ in 6 ml of chloroform there are slowly added, at ambient temperature, 3 ml of trifluoroacetic acid. After stirring for 12 hours, 1 equivalent of $NaN_3$ is added and the reaction mixture is held at ambient temperature for a further 12 hours. The reaction mixture is then washed with water and then with saturated NaCl solution and is dried over sodium sulphate. Chromatography over silica gel (dichloromethane/methanol: 95/5) allows the expected product to be isolated.

Step B: (±)-1-Amino-2-hydroxy-6-methoxy-3,3,14-trimethyl-2,3,7,14-tetrahydro-1H-benzo[b]pyrano[3,2-h]acridin-7-one A solution containing 0.2 g of the compound obtained in Step A and 0.09 g of Pd/C in 5 ml of ethanol is stirred at ambient temperature under an $H_2$ atmosphere for 48 hours. The catalyst is then filtered off and the filtrate is concentrated in vacuo. The residue is chromatographed over silica (dichloromethane/methanol: 95/5), allowing the desired product to be isolated.

Preparation 7

6-(Dimethylaminoethyloxy)-3,3,14-trimethyl-7,14-dihydro-3H-benzo-[b]pyrano[3,2-h]acridin-7-one Step A: 6-Hydroxy-3,3,14-trimethyl-7,14-dihydro-3H-benzo[b]pyrano[3,2-h]acridin-7-one The product is obtained according to the procedure of Preparation 1, using only 1.5 equivalents of sodium hydride and 2 equivalents of dimethyl sulphate.

Melting point: 138° C.

Step B. 6-(Dimethylaminoethyloxy)-3,3,14-trimethyl-7,14-dihydro-3H-benzo[b]-pyrano[3,2-h]acridin-7-one To a solution, under nitrogen, of 0.2 g of the compound obtained in Step A in 20 ml of dimethylformamide, there are added 1 equivalent of sodium hydride and 1 equivalent of 2-dimethylaminoethyl chloride hydrochloride. After 48 hours at 70° C., the reaction mixture is cooled; it is then poured onto 80 ml of ice-cold water and extracted with dichloromethane. After washing and drying over $MgSO_4$, the solution is evaporated under reduced pressure. Chromatography over silica gel (ethyl acetate/cyclohexane: 80/20) allows the expected product to be isolated.

Mass spectrum: (DIC/$NH_3$): m/z: 429 (M+H)$^+$

Preparation 8

1,2-Diamino-6-methoxy-3,3,14-trimethyl-2,3,7,14-tetrahydro-1H-benzo[b]pyrano[3,2-h]acridin-7-one Chromatography over silica gel allows isolation of this co-product, which forms during synthesis of the compound of Preparation 6.

EXAMPLE 1

6-(2-Hydroxyethoxy)-3,3,14-trimethyl-3,14-dihydro-7H-benzo[b]-pyrano[3,2-h]acridin-7-one A solution of 500 mg of the compound of Preparation 1 in 5 ml of dichloroethane in the presence of 36 mg of $AlCl_3$ is heated at 70° C. for 3 hours. The reaction mixture is then poured onto 10% HCl solution and extracted with dichloromethane. After conventional treatment of the organic phases and evaporation thereof under reduced pressure, chromatography of the residue over silica gel (dichloromethane/methanol: gradient from 0.2 to 10%) allows the expected product to be isolated.

Melting point: 230° C.

EXAMPLE 2

2-Butyryl-6-methoxy-3,3,14-trimethyl-3,14-dihydro-7H-benzo[b]-pyrano[3,2-h]acridin-7-one A mixture of 0.81 mmol of butyryl chloride and 0.673 mmol of $AlCl_3$ in 2 ml of anhydrous dichloromethane is added, in small portions, to 0.135 mmol of the product of Preparation 1 in 2 ml of dichloromethane at 0° C. The reaction mixture is stirred for 4 hours at ambient temperature and is then poured onto 10% HCl solution. After conventional treatment of the organic phases and evaporation thereof under reduced pressure, chromatography of the residue over silica gel (dichloromethane/methanol: gradient from 0.1 to 6%) allows the expected product to be isolated.

Melting point: 302° C.

EXAMPLE 3

2-Benzoyl-6-methoxy-3,3,14-trimethyl-3,14-dihydro-7H-benzo[b]-pyrano[3,2-h]acridin-7-one The product is obtained according to the procedure of Example 2, using benzoyl chloride as reagent.

Melting point: 319° C.

EXAMPLE 4

2-Acetyl-6-methoxy-3,3,14-trimethyl-3,14-dihydro-7H-benzo[b]-pyrano[3,2-h]acridin-7-one The product is obtained according to the procedure of Example 2, using acetyl chloride as reagent.

Melting point: 277° C.

EXAMPLE 5

2-Butylryl-6-(diethylaminopropylamino)-3,3,14-trimethyl-3,14-dihydro-7H-benzo[b]-pyrano[3,2-h]acridin-7-one The product is obtained according to the procedure of Example 2, using the compound of Preparation 3 as substrate.

EXAMPLE 6

2-Butyryl-6-[(2-morpholin-4-yl)ethylamino]-3,3,14-trimethyl-3,14-dihydro-7H-benzo[b]pyrano[3,2-h]acridin-7-one The product is obtained according to the procedure of Example 2, using the compound of Preparation 4 as substrate.

EXAMPLE 7

(±)-cis-1,2-Dipentenoyloxy-6-methoxy-3,3,14-trimethyl-2,3,7,14-tetrahydro-1H-benzo[b]pyrano[32-h]acridin-7-one A solution of 1.48 mmol of the compound of Preparation 2 in 15 ml of anhydrous pyridine is added to 14.8 mmol of pentenoyl chloride. The reaction mixture is stirred at ambient temperature for 6 hours and is then extracted with dichloromethane. The combined organic phases are dried over magnesium sulphate, filtered and then evaporated under reduced pressure. Chromatography of the residue over silica gel (dichloromethane/methanol: gradient from 0.2 to 2%) allows the expected product to be isolated.

Melting point: 152° C.

EXAMPLE 8

(±)-cis-1-Hydroxy-6methoxy-2-pentenoyloxy-3,3,14-trimethyl-2,3,7,14-tetrahydro-1H-benzo[b]pyrano[3,2-h]acridin-7-one The co-product is isolated during chromatography of the compound of Example 7 over silica gel.

Melting point: 194° C.

EXAMPLE 9

6-Methoxy-3,3,14-trimethyl-7-oxo-7,14-dihydro-3H-benzo[b]pyrano-[3,2-h]acridin-2-yl Butyrate Step 1: (±)-cis-1-Hydroxy-6-methoxy-3,3,14-trimethyl-7-oxo-2,3,7,14-tetrahydro-1H-benzo[b]pyrano[3,2-h]acridin-2-yl Butyrate To a solution of 0.74 mmol of the compound of Preparation 2 in 7 ml of anhydrous pyridine in the presence of 4-dimethylaminopyridine there are added 2 equivalents of butyryl chloride. The reaction mixture is stirred at ambient temperature. After 72 hours, 5 equivalents of butyryl chloride are added and the mixture is stirred for 72 hours and then evaporated to dryness. Chromatography over silica gel allows the expected product to be isolated.

Melting point: 197° C.

Step 2: 6-Methoxy-3,3,14-trimethyl-7-oxo-7,14-dihydro-3H-benzo[b]pyrano-[3,2-h]acridin-2-yl Butyrate To a solution of 0.29 mmol of the compound obtained in Step 1 in 6 ml of dichloromethane there are added 4 drops of 10% HCl solution. The reaction mixture is stirred at ambient temperature for 3 days and is then dried and evaporated under reduced pressure. Chromatography of the residue over silica gel (dichloromethane/methanol: gradient from 0.2 to 5%) allows the expected product to be isolated.

Melting point: 180° C.

EXAMPLE 10

6-Methoxy-3,3,14-trimethyl-7-oxo-7,14-dihydro-3H-benzo[b]pyrano-[3,2-h]acridin-2-yl Acetate Step 1: (±)-cis-1-Hydroxy-6-methoxy-3,3,14-trimethyl-7-oxo-2,3,7,14-tetrahydro-1H-benzo[b]pyrano-[3,2-h]acridin-2-yl Acetate The product is obtained according to the procedure of Step 1 of Example 9, using acetyl chloride as reagent.

Step 2: 6-Methoxy-3,3,14-trimethyl-7-oxo-7,14-dihydro-3H-benzo[b]pyrano-[3,2-h]acridin-2-yl Acetate The product is obtained according to the procedure of Step 2 of Example 9, using the compound obtained in Step 1 above as substrate.

Melting point: 165° C.

EXAMPLE 11

(1S,2S)-1-{[(Dimethylamino)carbonyl]oxy}-6-methoxy-3,3,14-trimethyl-7-oxo-2,3,7,14-tetrahydro-1H-benzo[b]pyrano[3,2-h]acridin-2-yl Dimethylcarbamate In a flask, 0.698 mmol of potassium hydride is washed three times with hexane and then cooled to −10° C., and a solution of 0.123 mmol of the compound of Preparation 2 in 4 ml of anhydrous tetrahydrofuran is added. After the dropwise addition of 0.327 mmol of N,N-dimethylcarbamoyl chloride at −10° C., stirring is carried out for 3 hours 30 minutes at ambient temperature. The reaction is stopped by adding 50 ml of ethyl acetate and 10 ml of saturated $NaHCO_3$ solution in order to obtain a pH of 8. The organic phase is washed with water and dried over magnesium sulphate. After evaporation under reduced pressure and crystallisation from ethyl acetate, the expected product is isolated.

Melting point: 173° C.

EXAMPLE 12

(1S,2S)-6-Methoxy-3,3,14-trimethyl-2-{[(4-methylphenyl)sulphonyl]-oxy}-7-oxo-2,3,7,14-tetrahydro-1H-benzo[b]pyrano[3,2-h]acridin-1-yl 4-methylbenzenesulfonate The product is obtained according to the procedure of Example 11, using tosyl chloride as reagent.

EXAMPLE 13

(1S,2S)-6-{[3-(Diethylamino)propyl]amino}-1-{[(dimethylamino)-carbonyl]oxy}-3,3,14-trimethyl-7-oxo-2,3,7,14-tetrahydro-1H-benzo[b]pyrano[3,2-h]acridin-2-yl Dimethylcarbamate The product is obtained according to the procedure of Example 11, Steps 1 to 2, using the product of Preparation 5 as substrate.

EXAMPLE 14

(1S,2S)-1-{[(Dimethylamino)carbonyl]amino}-6-methoxy-3,3,14-trimethyl-7-oxo-2,3,7,14-tetrahydro-1H-benzo[b]pyrano[3,2-h]acridin-2-yl Dimethylcarbamate The product is obtained according to the procedure of Example 11, Steps 1 to 2, using the product of Preparation 6 as substrate.

EXAMPLE 15

N'-((1S,2S)-1-{[(Dimethylamino)carbothioyl]amino}-6-methoxy-3,3,14-trimethyl-7-oxo-2,3,7,14-tetrahydro-1H-benzo[b]pyrano[3,2-h]acridin-2-yl)-N,N-dimethylthiourea The product is obtained according to the procedure of Example 11, Steps 1 to 2, using the product of Preparation 8 as substrate and dimethylthiocarbamoyl chloride as reagent.

EXAMPLE 16

6-[2-(Dimethylamino)ethoxy]-3,3,14-trimethyl-7-oxo-7,14-dihydro-3H-benzo[b]pyrano[3,2-h]acridin-2-yl Butyrate The product is obtained according to the procedure of Steps 1 to 2 of Example 9, using the compound of Preparation 7 as substrate in Step 1.

EXAMPLE 17

13-Amino-6-methoxy-3,3,14-trimethyl-3,14-dihydro-7H-benzo[b]-pyrano[3,2-h]acridin-7-one Step 1: 3-Acetamido-4-nitro-2-naphthalenecarboxylic Acid A solution of 5 g of 3-amino-2-naphthalenecarboxylic acid in 40 ml of acetic anhydride is stirred at ambient temperature for 30 minutes and then 5 ml of nitric acid are added dropwise. The reaction mixture is then stirred in an ice bath for 7 days and is then poured onto ice. The precipitate formed is filtered off, washed with water and then dried and rinsed with 40 ml of methanol, allowing the expected product to be isolated after drying.

Melting point: 235° C.

Step 2: 3-Amino-4-nitro-2-naphthalenecarboxylic Acid

A solution of 1 g of the compound obtained in Step 1 in 18 ml of hydrochloric acid is refluxed for 4 hours and then poured onto ice. The precipitate formed is filtered off, washed with water until the pH is 5–6 and then dried, allowing the expected product to be isolated.

Melting point: 238° C.

Step 3: 3-Chloro-4-nitro-2-naphthalenecarboxylic Acid 1.2 g of sodium nitrite are slowly added to 13 ml of concentrated sulphuric acid; the temperature is brought to 70° C. until the sodium nitrite has dissolved completely; the solution is then cooled to 20° C.

A solution of 3 g of the compound obtained in Step 2 above in 27 ml of acetic acid is cautiously added to the reaction mixture. The solution is then heated at 40° C. for 30 minutes and is then cooled in an ice bath.

A solution of cuprous chloride (3.3 g) in 30 ml of concentrated hydrochloric acid is cooled in an ice bath and the solution of the diazoic compound previously obtained is slowly added. The temperature of the reaction mixture is then brought to 80° C. and the reaction mixture is stirred until the evolution of gas has ceased.

Water is added to the reaction mixture, whilst cooling the latter in an ice bath. The precipitate formed is filtered off, carefully rinsed with water and dried. Crystallisation from dichloromethane allows the expected product to be obtained.

Melting point: 246° C.

Step 4: 3-[(2,2-Dimethyl-7-methoxy-2H-chromen-5-yl) amino]-4-nitro-2-naphthalene-carboxylic Acid To 3.3 g of 5-amino-7-methoxy-2,2-dimethylchromene there are added 3 g of the compound obtained in Step 3 above, 3.4 g of potassium acetate, 375 mg of $Cu(OAc)_2.H_2O$ and 120 ml of 2-propanol containing 3.8 ml of triethylamine. The solution is refluxed for 5 days and is then evaporated under reduced pressure. The residue is taken up in a 1/1 mixture of dichloromethane and 1N aqueous HCl solution. After extraction of the aqueous phase, the combined organic phases are treated in customary manner. Chromatography over silica gel (dichloromethane/methanol: gradient from 0.1 to 1%) allows the expected product to be isolated.

Melting point: 165° C.

Step 5: 6-Methoxy-3,3-dimethyl-13-nitro-3,14-dihydro-7H-benzo[b]pyrano[3,2-h]-acridin-7-one 772 mg of the compound obtained in Step 4 are dissolved in 45 ml of anhydrous dichloromethane, and 3 ml of trifluoroacetic anhydride are added. After stirring for 5 minutes at ambient temperature, the reaction mixture is evaporated. The residue is taken up in a mixture of dichloromethane and saturated $NaHCO_3$ solution. After extraction of the aqueous phase with dichloromethane, the combined organic phases are treated in conventional manner and then distilled, allowing the expected product to be isolated.

Melting point: >350° C.

Step 6: 6-Methoxy-3,3,14-trimethyl-13-nitro-3,14-dihydro-7H-benzo[b]pyrano-[3,2-h]acridin-7-one To a solution of 300 mg of the compound obtained in Step 5 in 30 ml of dimethylformamide there are added 1.48 g of sodium hydride and then 1.8 ml of iodomethane. The reaction mixture is refluxed, under argon, for 3 days, and is then slowly hydrolysed by the addition of ice. The precipitate formed is filtered off and then dried and is chromatographed over silica gel (dichloromethane/methanol: gradient from 0.1 to 0.5%), allowing the expected product to be isolated.

Melting point: 283° C.

Step 7: 13-Amino-6-methoxy-3,3,14-trimethyl-3,14-dihydro-7H-benzo[b]pyrano-[3,2-h]acridin-7-one To 178 mg of the compound obtained in Step 6 above in 10 ml of acetic acid and 1 ml of water there are added 621 mg of zinc wool. The reaction mixture is stirred at ambient temperature for 2.5 hours and is then filtered. The filtrate is made alkaline using 10% aqueous ammonium hydroxide solution; the precipitate formed is then separated off by filtration. The crude residue is purified by chromatography over silica gel (dichloromethane/methanol: gradient from 0.1 to 0.5%), allowing the expected product to be isolated.

Melting point: 157° C.

EXAMPLE 18

2,2,2-Trifluoro-N-(6-methoxy-3,3,14-trimethyl-7-oxo-7,14-dihydro-3H-benzo[b]pyrano[3,2-h]acridin-13-yl)acetamide A solution of 0.039 mmol of the compound obtained in Example 17 in 7 ml of anhydrous pyridine, under argon, is stirred at −20° C., and 0.15 mmol of trifluoroacetic anhydride is added. The reaction mixture is stirred for 6 hours at −20° C. and is then diluted with 15 ml of methanol and concentrated under reduced pressure. Chromatography of the residue over silica gel (dichloromethane/methanol: 99.9/0.1) allows the expected product to be isolated.

EXAMPLE 19

N-(6-Methoxy-3,3,14-trimethyl-7-oxo-7,14-dihydro-3H-benzo[b]-pyrano[3,2-h]acridin-13-yl)acetamide The product is obtained according to the procedure of Example 18, using acetic anhydride as reagent.

EXAMPLE 20

6-Methoxy-3,3,14-trimethyl-1,7-dioxo-2,3,7,14-tetrahydro-1H-benzo[b]pyrano[3,2-h]acridin-2-yl Acetate Step 1: 2-Hydroxy-6-methoxy-3,3,14-trimethyl-2,3-dihydro-1H-benzo[b]pyrano-[3,2-h]acridine-1,7(14H)-dione A suspension of 1.28 g of $KMnO_4$ in 15 ml of water is added dropwise, over 30 minutes, to a solution of 0.5 g of the product of Preparation 1 dissolved in 25 ml of acetone. The reaction mixture is stirred at ambient temperature for 8 hours and is then extracted with 2-butanone. The organic phase is treated in conventional manner and chromatography of the residue over silica gel (dichloromethane/methanol: 98/2) allows the expected product to be isolated.

Melting point: 272° C.

Step 2: 6-Methoxy-3,3,14-trimethyl-1,7-dioxo-2,3,7,14-tetrahydro-1H-benzo-[b]pyrano[3,2-h]acridin-2-yl Acetate The product is obtained according to the procedure of Step 1 of Example 9, using acetic anhydride as reagent.

Melting point: 206° C.

EXAMPLE 21

6-Methoxy-3,3,14-trimethyl-1,7-dioxo-2,3,7,14-tetrahydro-1H-benzo[b]pyrano[3,2-h]acridin-2-yl Propionate The product is obtained according to the procedure of Example 20, using propionic anhydride as reagent in Step 2.

Melting point: 218° C.

EXAMPLE 22

6Methoxy-3,3-dimethyl-1,7-dioxo-2,3,7,14-tetrahydro-1H-benzo-[b]pyrano[3,2-h]acridin-2-yl Acetate Step 1: 3-[(8-Methoxy-2,2-dimethyl-2H-chromen-5-yl)amino]-2-naphthoic Acid A solution containing 1.2 mmol of 3-bromonaphthalene-2-carboxylic acid, 1.19 mmol of 7-methoxy-2,2-dimethyl-2H-1-benzopyran-5-ylamine, 2.38 mmol of potassium acetate, 10 mg of $Cu(OAc)_2 \cdot H_2O$ and 1.19 mmol of triethylamine in 17 ml of 2-propanol is refluxed for 24 hours and then concentrated under reduced pressure. The residue obtained is taken up in a 2/1 mixture of dichloromethane/1N HCl. The aqueous phase is extracted with dichloromethane and the combined organic phases are then treated in conventional manner. Chromatography of the residue over silica gel (dichloromethane) allows the expected product to be isolated.

Step 2: 6-Methoxy-3,3-dimethyl-3,14-dihydro-7H-benzo[b]pyrano[3, 2-h]acridin-7-one To a solution containing 1.94 mmol of the compound obtained in Step 1 in 20 ml of anhydrous dichloromethane, maintained at 0° C. under argon, there are added 9.71 mmol of trifluoroacetic anhydride. After reacting for 3 days at ambient temperature, the reaction mixture is concentrated under reduced pressure. The residue is taken up in a mixture of dichloromethane and aqueous $NaHCO_3$ solution. After extraction with dichloromethane, the combined organic phases are treated in conventional manner. Chromatography of the residue over silica gel (dichloromethane) allows the expected product to be isolated, the latter being subsequently recrystallised from ethyl ether.

Melting point: 278° C.

Step 3: 2-Hydroxy-6-methoxy-3,3-dimethyl-2,3-dihydro-1H-benzo[b]pyrano[3,2-h]-acridine-1,7(14H)-dione To a solution of 1.33 mmol of the compound obtained in Step 2 in 30 ml of a 10/3/1 mixture of tert-butanol/tetrahydrofuran/water there are added osmium tetroxide in the form of a 2.5% solution in 0.67 ml of 2-methyl-2-propanol and 1.35 mmol of 4-methylmorpholine-N-oxide monohydrate. After stirring for two days at ambient temperature, $NaHSO_3$ solution is added. After stirring for one hour, the reaction mixture is extracted with dichloromethane. The organic phase is dried, filtered and then evaporated under reduced pressure. Chromatography of the residue over silica gel (dichloromethane/methanol: 98/2) allows the expected product to be isolated.

Melting point: 230° C.

Step 4: 6-Methoxy-3,3-dimethyl-1,7-dioxo-2,3,7,14-tetrahydro-1H-benzo-[b]pyrano[3,2-h]acridin-2-yl Acetate The product is obtained according to the procedure of Step 2 of Example 20, using an excess of acetic anhydride.

Melting point: 206° C.

EXAMPLE 23

(±)-cis-1-{[(Diethylamino)carbonyl]oxy}-6-methoxy-3,3,14-trimethyl-7-oxo-2,3,7,14-tetrahydro-1H-benzo[b]pyrano[3,2-h]acridin-2-yl Diethylcarbamate The product is obtained according to the procedure of Example 11, using N,N-diethylcarbamoyl chloride as reagent.

Melting point: 193° C.

EXAMPLE 24

(±)-cis-1-{[(Diisopropylamino)carbonyl]oxy}-6-methoxy-3,3,14-trimethyl-7-oxo-2,3,7,14-tetrahydro-1H-benzo[b]pyrano[3,2-h]acridin-2-yl Diisopropylcarbamate The product is obtained according to the procedure of Example 11, using N,N-diisopropylcarbamoyl chloride as reagent.

Melting point: 149.5° C.

EXAMPLE 25

(±)cis-1-{[(Dibutylamino)carbonyl]oxy}-6-methoxy-3,3,14-trimethyl-7-oxo-2,3,7,14-tetrahydro-1H-benzo[b]pyrano[3,2-h]acridin-2-yl Dibutylcarbamate The product is obtained according to the procedure of Example 11, using N,N-dibutylcarbamoyl chloride as reagent.

Melting point: 138° C.

EXAMPLE 26

6Methoxy-3,3-dimethyl-1,7-dioxo2,3,7,14-tetrahydro-1H-benzo-[b]pyrano[3,2-h]acridin-2-yl Propionate To a previously cooled solution of anhydrous pyridine (1.5 ml) and an excess of propionic anhydride there is added 0.26 mmol of the compound obtained in Step 3 of Example 22. The reaction mixture is stirred at ambient temperature, protected from light, for 24 hours and is then poured onto ice-cold water (10 ml). The precipitate obtained is filtered off, washed with water and dried under a phosphoric vacuum. Chromatography of the residue over silica gel (dichloromethane) allows the expected product to be isolated.

Melting point: 231° C.

Pharmacological Study of Compounds of the Invention

EXAMPLE 27

In Vitro Activity

Murine leukaemia L1210 was used in vitro. The cells are cultured in RPMI 1640 complete culture medium containing 10% foetal calf serum, 2 mM glutamine, 50 units/ml of penicillin, 50 µg/ml of streptomycin and 10 mM Hepes, pH: 7.4. The cells are distributed on microplates and exposed to the cytotoxic compounds for 4 doubling periods, or 48 hours. The number of viable cells is then quantified by means of a colorimetric assay, the Microculture Tetrazolium Assay (J. Carmichael et al., Cancer Res., 47, 936–942, (1987)). The results are expressed as $IC_{50}$, the concentration of cytotoxic agent which inhibits the proliferation of the treated cells by 50%.

By way of illustration, the compounds of Examples 11 and 7 exhibit an $IC_{50}$ of 0.78 µM and 0.52 µM, respectively, thereby demonstrating their greater activity than the reference compound (acronycine).

EXAMPLE 28

In Vitro Activity
1—Anti-Tumour Activity with Respect to P388 Leukaemia
Line P388 (murine leukaemia) was supplied by the National Cancer Institute (Frederick, USA). The tumour cells ($10^6$ cells) were inoculated on day 0 into the peritoneal cavity of female B6D2F1 mice (Iffa Credo, France). Six mice weighing from 18 to 20 g were used in each test group. The products were administered by the intravenous route on day 1. The anti-tumour activity is expressed as % T/C:

$$\% \ T/C(\text{mouse}) = \frac{\text{Median survival time of the treated animals}}{\text{Median survival time of the control animals}} \times 100$$

The compounds of the present invention are very active in this model, having a T/C of >150%, whereas acronycine is only marginally active.
2—Anti-Tumour Activity with Respect to C38 Adenocarcinoma of the Colon
Tumour fragments of C38 adenocarcinoma of the colon weighing approximately 30 mg were implanted under the skin of B6D2F1 mice (Iffa Credo, France) on day 0. After growth of the tumour, the mice were divided into control (18 animals) and treated (6 or 7 animals) groups, which were homogeneous with respect to tumour size. The products were administered by the i.v. route once per week for 3 weeks (on days 10, 17 and 24), at their Maximum Tolerated Dose (MTD), MTD/2 and MTD/4.

The tumours were measured twice a week and the tumour volumes were calculated according to the following formula: volume ($mm^3$)=length (mm)×breadth ($mm^2$)/2. The anti-tumour activity is expressed as % T/C:

$$\% \ T/C = \frac{\text{median } Vt/V0 \text{ of the treated animals}}{\text{median } Vt/V0 \text{ of the control animals}} \times 100$$

V0 and Vt being the initial volume of the tumour and its volume at measurement time t, respectively.

The optimum dose is the dose giving the lowest T/C value without toxicity (early death or weight loss greater than 20%).

By way of example, the compounds of Examples 7 and 11 exhibit an anti-tumour activity of 30% for an optimum dose of 12.5 mg/kg and 41% for an optimum dose of 25 mg/kg, respectively, whereas acronycine exhibits an anti-tumour activity of 27% for an optimum dose of 100 mg/kg, thereby demonstrating their strong therapeutic potential.

EXAMPLE 29

Pharmaceutical Composition: Injectable Solution

| | |
|---|---|
| Compound of Example 11 | 10 mg |
| Distilled water for injectable preparations | 25 ml |

What is claimed is:
1. A compound selected from those of formula (I):

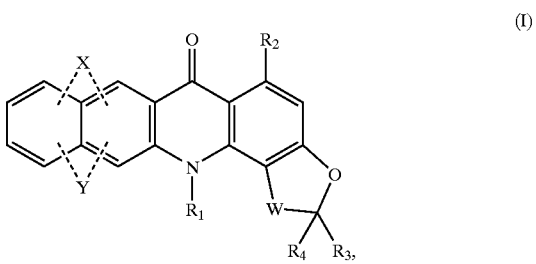

wherein:
X and Y, which may be the same or different, represent, independently of one another, a group selected from:
hydrogen and halogen,
mercapto, cyano, nitro, linear or branched ($C_1$–$C_6$) alkyl, linear or branched ($C_1$–$C_6$)-trihaloalkyl and linear or branched trihalo-($C_1$–$C_6$)alkyl-carbonylamino,
groups of formulae —ORa, —NRaRb, —NRa—C(O)-$T_1$, —O—C(O)—$T_1$, —O-$T_2$—NRaRb, —O-$T_2$-ORa, —NRa-$T_2$-NRaRb, —NRa-$T_2$-ORa and —NRa-$T_2$-$CO_2$Ra wherein:
Ra represents a group selected from hydrogen and linear or branched ($C_1$–$C_6$) alkyl, aryl and aryl-($C_1$–$C_6$)alkyl wherein the alkyl moiety is linear or branched,
Rb represents a group selected from hydrogen and linear or branched ($C_1$–$C_6$) alkyl, aryl and aryl-($C_1$–$C_6$)alkyl wherein the alkyl moiety is linear or branched, or
Ra+Rb, together with the nitrogen atom carrying them, form a monocyclic 5- or 6-membered heterocycle optionally containing in the cyclic system a second hetero atom selected from oxygen and nitrogen,
$T_1$ represents a group selected from linear or branched ($C_1$–$C_6$) alkyl, linear or branched ($C_2$–$C_6$) alkenyl, aryl, aryl-($C_1$–$C_6$)alkyl (wherein the alkyl moiety is linear or branched), and linear or branched ($C_1$–$C_6$) alkylene substituted by a group selected from —ORa and —NRaRb wherein Ra and Rb are as defined hereinbefore,
$T_2$ represents linear or branched ($C_1$–$C_6$) alkylene, it being understood that the substituents X and Y may be present on either of the two adjacent benzene rings,
$R_1$ represents hydrogen or linear or branched ($C_1$–$C_6$) alkyl,
$R_2$ represents a group selected from hydrogen and linear or branched ($C_1$–$C_6$) alkyl, —ORa, —NRaRb, —NRa—C(O)-T$_1$, —O—C(O)-T$_1$, —O-T$_2$-NRaRb, —O-T$_2$-ORa, —NRa-T$_2$-NRaRb, —NRa-T$_2$-ORa and —NRa-T$_2$-CO$_2$Ra, wherein Ra, Rb, T$_1$ and T$_2$ are as defined hereinbefore, R$_3$, R$_4$, which may be the same or different, represent, independently of one another, hydrogen or linear or branched (C$_1$–C$_6$) alkyl, W represents a group of formula —CH(R$_5$)—CH(R$_6$)—, —CH=C(R$_7$)—, —C(R$_7$)=CH— or —C(O)—CH(R$_8$)— wherein:

R$_5$ and R$_6$ represent, independently of the other, a group selected from —W$_1$—C(W$_2$)— —W$_4$—C(W$_2$)-T'$_1$, —W$_1$—S(O)$_n$—W$_3$-T$_1$ and —W$_1$—S(O)$_n$-T$_1$ wherein:

W$_1$ represents oxygen or sulphur or nitrogen substituted by hydrogen or by linear or branched (C$_1$–C$_6$) alkyl, aryl or aryl-(C$_1$–C$_6$)alkyl wherein the alkyl moiety is linear or branched, W$_2$ represents oxygen or sulphur, W$_3$ represents oxygen or sulphur or nitrogen substituted by hydrogen or by linear or branched C$_1$–C$_6$ alkyl, aryl or aryl-(C$_1$–C$_6$)alkyl wherein the alkyl moiety is linear or branched, a bond when T$_1$ represents linear or branched (C$_2$–C$_6$) alkenyl, W$_4$ represents sulphur or nitrogen substituted by hydrogen or by linear or branched (C$_1$–C$_6$)alkyl, aryl or aryl-(C$_1$–C$_6$)alkyl wherein the alkyl moiety is linear or branched, T$_1$ is as defined hereinbefore, T'$_1$ represents a group selected from linear or branched (C$_2$–C$_6$) alkenyl, aryl, aryl-(C$_1$–C$_6$)alkyl (wherein the alkyl moiety is linear or branched), linear or branched (C$_1$–C$_6$) alkylene substituted by a group selected from —ORa and —NRaRb wherein Ra and Rb are as defined hereinbefore, n represents an integer selected from 1 and 2, alternatively, one of R$_5$ and R$_6$ represents, independently of the other, a group as defined hereinbefore and the other represents a group selected from hydrogen, hydroxy, linear or branched (C$_1$–C$_6$) alkoxy, linear or branched (C$_1$–C$_6$)alkyl-carbonyloxy, arylcarbonyloxy, aryl-(C$_1$–C$_6$)alkyl-carbonyloxy (wherein the alkyl moiety is linear or branched), and amino optionally substituted by one or two, identical or different, linear or branched (C$_1$–C$_6$)alkyl, R$_7$ represents a group selected from hydroxy, linear or branched (C$_1$–C$_6$) alkoxy, —C(W$_2$)-T$_1$, —W$_1$—C(W$_2$)—W$_3$-T$_1$, —W$_1$—C(W$_2$)-T$_1$, —W$_1$—S(O)$_n$—W$_3$-T$_1$ and —W$_1$—S(O)$_n$-T$_1$ wherein W$_1$, W$_2$, W$_3$, T$_1$ and n are as defined hereinbefore, or R$_7$ may represent hydrogen when R$_2$ represents —O—T$_2$-ORa and/or when X represents hydrogen and Y, located in the 13-position of the naphthyl system of the pentacyclic skeleton, represents amino optionally substituted by one or two identical or different groups selected independently of one another from linear or branched (C$_1$–C$_6$)alkyl, linear or branched (C$_1$–C$_6$)acyl and linear or branched trihalo-(C$_1$–C$_6$) alkyl-carbonyl, R$_8$ represents linear or branched (C$_1$–C$_6$) alkoxy or linear or branched (C$_1$–C$_6$)alkyl-carbonyloxy, or may have the additional meaning of hydroxy when R$_2$ represents —O-T$_2$-ORa as defined hereinbefore, its enantiomers, diastereoisomers, N-oxides, and addition salts thereof with a pharmaceutically acceptable acid or base, wherein:

aryl being understood to mean phenyl or naphthyl optionally containing one or more, identical or different, substituents selected from hydroxy, halogen, carboxy, nitro, amino, linear or branched (C$_1$–C$_6$) lkylamino, di(C$_1$–C$_6$) alkylamino, wherein each alkyl moiety may be linear or branched, linear or branched (C$_1$–C$_6$) alkoxy, linear or branched (C$_1$–C$_6$)acyl and linear or branched (C$_1$–C$_6$)alkyl-carbonyloxy, and optical isomers thereof.

2. A compound of claim 1, selected from those of formula (IA):

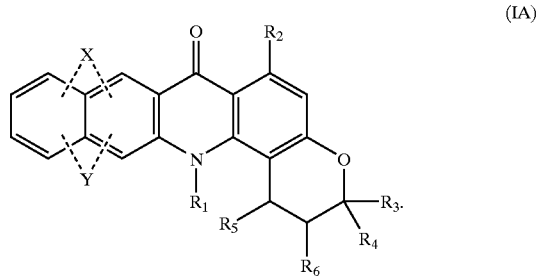

(IA)

3. A compound of claim 2, wherein R$_5$ and R$_6$ are identical and each represent a group of formula —W$_1$—C(W$_2$)—W$_3$-T$_1$ or —W$_1$—S(O)$_n$-T$_1$.

4. A compound of claim 2, wherein R$_5$ and R$_6$ are identical and each represent a group of formula —W$_1$—C(W$_2$)—W$_3$-T$_1$, wherein W$_1$ represents oxygen, W$_2$ represents oxygen, represents nitrogen substituted by hydrogen, linear or branched (C$_1$–C$_6$)alkyl, aryl or aryl-(C$_1$–C$_6$)alkyl, wherein the alkyl moiety is linear or branched.

5. A compound of claim 2, wherein R$_5$ and R$_6$ are identical and each represent a group of formula —W$_1$—S(O)$_n$-T$_1$, wherein W$_1$ represents oxygen, and n is 2.

6. A compound of claim 1, selected from those of formula (IB):

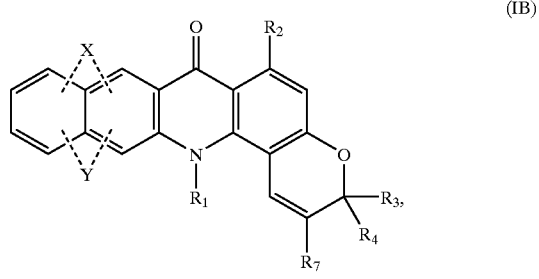

(IB)

7. A compound of claim 6, wherein R$_7$ represents a group selected from —C(W$_2$)-T$_1$ and —W$_1$—C(W$_2$)-T$_1$.

8. A compound of claim 7, wherein W$_1$ represents oxygen, W$_2$ represents oxygen and T$_1$ represents linear or branched (C$_1$–C$_6$)alkyl, aryl or aryl-(C$_1$–C$_6$)alkyl, wherein the alkyl moiety is linear or branched.

9. A compound of claim 1, selected from those of formula (IC):

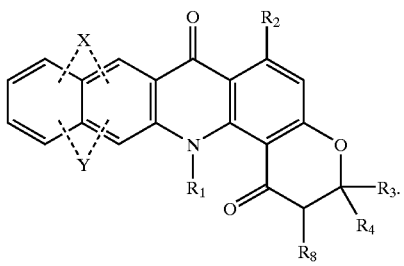

(IC)

10. A compound of claim 1, wherein $R_3$ and $R_4$, which may be the same or different, represent linear or branched $(C_1-C_6)$alkyl.

11. A compound of claim 1, wherein $R_2$ represents a group selected from linear or branched $(C_1-C_6)$ alkoxy, —NRaRb, —O—$T_2$-NRaRb, —O-$T_2$-ORa, —NRa-$T_2$-NRaRb and —NRa-$T_2$-ORa.

12. A compound of claim 1, selected from those of formula $(IB_1)$:

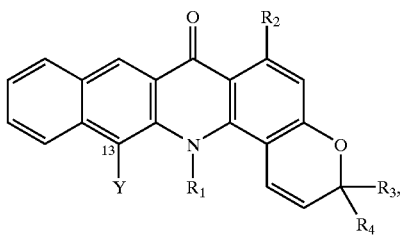

$(IB_1)$ wherein Y represents amino optionally substituted by one or two identical or different groups selected independently of one another from linear or branched $(C_1-C_6)$alkyl, linear or branched $(C_1-C_6)$ acyl, and linear or branched trihalo-$(C_1-C_6)$alkyl-carbonyl.

13. A compound of claim 1, which is:
- (1S,2S)-1-{[(dimethylamino)carbonyl]oxy}-6-methoxy-3,3,14-trimethyl-7-oxo-2,3,7,14-tetrahydro-1H-benzo[b]pyrano[3,2-h]acridin-2-yl dimethylcarbamate, or
- (1S,2S)-6-methoxy-3,3,14-trimethyl-2-{[(4-methylphenyl)sulphonyl]oxy}-7-oxo-2,3,7,14-tetrahydro-1H-benzo[b]pyrano[3,2-h]acridin-1-yl 4-methylbenzenesulfonate, its enantiomer, diastereoisomer, N-oxide, or an addition salt thereof with a pharmaceutically acceptable acid or base.

14. A compound of claim 1, selected from:
- -6-methoxy-3,3,14-trimethyl-7-oxo-7,14-dihydro-3H-benzo[b]pyrano[3,2-h]acridin-2-yl acetate,
- 2-benzoyl-6-methoxy-3,3,14-trimethyl-3,14-dihydro-7H-benzo[b]pyrano[3,2-h]-acridin-7-one,
- 2-butyryl-6-methoxy-3,3,14-trimethyl-3,14-dihydro-7H-benzo [b]pyrano[3,2-h]-acridin-7-one,
- 2-acetyl-6-methoxy-3,3,14-trimethyl-3,14-dihydro-7H-benzo[b]pyrano[3,2-h]-acridin-7-one,
- 6-methoxy-3,3,14-trimethyl-7-oxo-7,14-dihydro-3H-benzo[b]pyrano[3,2-h]acridin-2-yl butyrate,
- 6-(2-hydroxyethoxy)-3,3,14-trimethyl-3,14-dihydro-7H-benzo [b]pyrano[3,2-h]-acridin-7-one,
- 13-amino-6-methoxy-3,3,14-trimethyl-3,14-dihydro-7H-benzo[b]pyrano[3,2-h]-acridin-7-one, or
- N-(6-methoxy-3,3,14-trimethyl-7-oxo-7,14-dihydro-3H-benzo[b]pyrano[3,2-h]-acridin-13-yl)acetamide, its enantiomer, diastereoisomer, N-oxide, or an addition salt thereof with a pharmaceutically acceptable acid or base.

15. A compound of claim 1, which is 6-methoxy-3,3-dimethyl-1,7-dioxo-2,3,7,14 tetrahydro-1H-benzo[b]pyrano [3,2-h]acridin-2-yl acetate, its enantiomer, diastereoisomer, N-oxide, or an addition salt thereof with a pharmaceutically acceptable acid or base.

16. A method for treating a living animal body afflicted with a cancer selected from leukemia and adenocarcinoma, comprising the step of administering to the living animal body an amount of a compound of claim 1, which is effective for alleviation of the cancer.

17. A pharmaceutical composition comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,642,248 B2  Page 1 of 1
DATED : November 4, 2003
INVENTOR(S) : Michel Koch et al.

It is certified that error appears in the above-identified patent and that said Letters Patent is hereby corrected as shown below:

Title page,
Item [73], Assignee, "Les Laboratories Servier" should be -- Les Laboratoires Servier --.

Column 31,
Line 12, insert -- $W_3$-$T_1$ -- after "-$W_1$-C($W_2$)-".
Line 21, "$C_1$-$C_6$)" should be -- ($C_1$-$C_6$) --.

Column 32,
Line 6, "lkylamino" should be -- alkylamino --.
Line 36, insert -- $W_3$ -- after "represents oxygen,".

Signed and Sealed this

Twenty-fifth Day of May, 2004

JON W. DUDAS
*Acting Director of the United States Patent and Trademark Office*